United States Patent [19]
Thompson

[11] 3,953,900
[45] May 4, 1976

[54] ARTIFICIAL LIMB WITH THREE-PART COSMETIC COVERING

[75] Inventor: Herbert Thompson, Harrow, England

[73] Assignee: Chas. A. Blatchford & Sons, Ltd., Basingstohe, England

[22] Filed: Feb. 25, 1975

[21] Appl. No.: 553,009

[30] Foreign Application Priority Data
Feb. 26, 1974 United Kingdom ................ 8582/74

[52] U.S. Cl. .............................................. 3/2; 3/12
[51] Int. Cl.² ........................ A61F 1/08; A61F 1/06
[58] Field of Search ........................... 3/2, 12–12.8, 3/22–29, 21

[56] References Cited
UNITED STATES PATENTS
2,422,302  6/1947  Horn ........................................ 3/12

FOREIGN PATENTS OR APPLICATIONS
497,032  8/1954  Italy ............................................. 3/2
66,257   4/1969  Germany ................................... 3/27

OTHER PUBLICATIONS
Orthotics & Prosthetics, Vol. 23, No. 1, Mar. 1969, pp. 54–61.
Bulletin of Prosthetic Research, BPR10-21, Spring 1974, pp. 72–73.

Primary Examiner—Ronald L. Frinks
Attorney, Agent, or Firm—Woodard, Weikart, Emhardt & Naughton

[57] ABSTRACT

An artificial limb of the endoskeletal type has an outer cosmesis or covering in two or more parts, whereby a worn or damaged part can be removed and replaced without the expense of replacing the complete outer cosmesis.

11 Claims, 3 Drawing Figures

ARTIFICIAL LIMB WITH THREE-PART COSMETIC COVERING

FIELD OF THE INVENTION

This invention relates to an artificial limb of the kind in which the structural parts are virtually entirely enclosed by material, preferably plastics material, shaped externally to conform to the general shape of a natural limb. This kind of artificial limb is referred to in the art as endo-skeletal.

DESCRIPTION OF THE PRIOR ART

It is known to envelop the structural parts of an artificial limb virtually wholly in a continuous outer covering or cosmesis, but this practice is comparatively recent. Before the continuous outer covering or cosmesis became known, any outer covering had a gap at the knee or elbow zone.

In a known continuous outer covering of an endo-skeletal artificial leg the structural parts are covered with a relatively thick-walled tube of plastics material, for example of a flexible polyurethane foam. When this tube is positioned on the leg structure, (for example covering the shin zone, the knee zone, and as much of the thigh zone as is necessary) it can be shaped to the required shape by removal of some of the plastics material.

In use of this known leg, this continuous outer covering is required to flex at the knee zone and the problem arises that, in time, with continual flexing and with rubbing against the contained structural parts, the covering in the knee zone becomes worn or damaged. Then the whole covering must be removed and a new tube must be fitted and shaped to form the new covering. This is expensive and time consuming.

SUMMARY OF THE INVENTION

To solve this problem, an artificial limb of the endo-skeletal kind is characterised in that the covering comprises two or more separable tubular parts, such that when one of the tubular parts becomes worn or damaged, the said one part can be removed and replaced. Preferably the covering is in three parts: in the case of a leg, one part over the shin and terminating below the knee; a second part over the knee zone and terminating above the knee; and a third part extending upwards on the thigh above the knee zone. These three parts would be fitted on to the leg structure separately. Adjacent ends of the parts of the covering would be in contact to avoid gaps. The whole may be sheathed in known manner in a skin of for example nylon stockinette.

The invention also includes a method of making an artificial leg comprising the steps of providing connected thigh, knee and shin structures; applying an upper outer covering part of tubular plastics material to the thigh structure; applying a middle outer covering part of tubular plastics material to the knee structure; applying a lower outer covering part of tubular plastics material to the shin structure; and causing the three parts to abut at their respective adjacent ends.

BRIEF DESCRIPTION OF THE DRAWINGS

The invention will now be described in more detail by way of example, with reference to the accompanying drawings, all three Figures of which are diagrammatic longitudinal sections, with some parts shown in elevation, of an artificial leg in accordance with the invention.

DESCRIPTION OF THE PREFERRED EMBODIMENT

Figure 1:
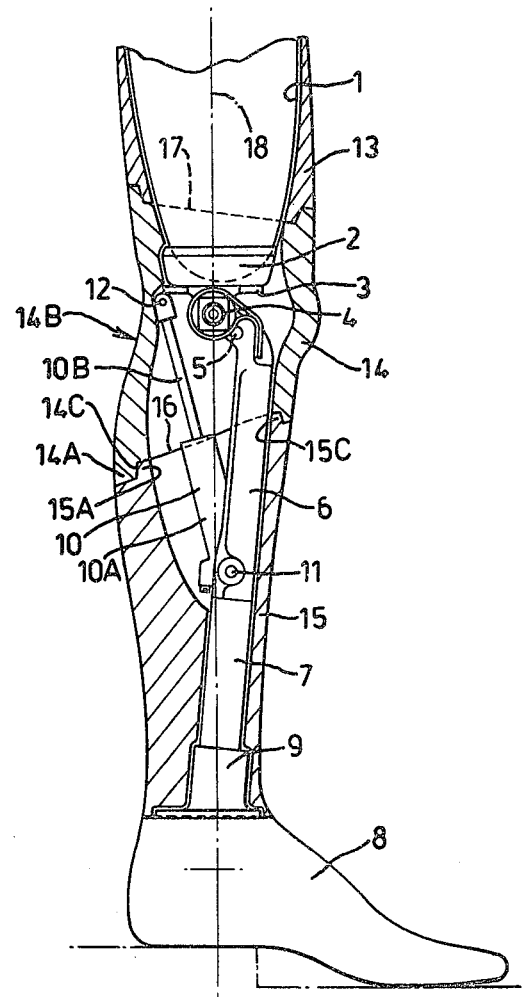
FIG. 1 shows the leg upright.

Referring to FIG. 1, an artificial leg has a thigh socket 1 mounted by a cup 2 on a plate 3 connected to a knee pivot structure 4. The structure 4 is connected at 5 to a bifurcated member 6 the lower end of which is connected to a shin tube 7. A foot 8 is connected by an adaptor 9 to the lower end of the shin tube 7. A pneumatic flexion control device 10 has a cylinder 10A, connected by a pivot 11 to the bifurcated member 6, and a piston rod 10B, connected by a pivot 12 to the knee pivot structure 4 by means not shown. These internal parts of the leg are conventional and are shown diagrammatically.

The leg has a continuous outer covering or cosmesis which is in three parts: an upper part 13; a middle part 14; and a lower part 15. These three parts are tubular and of plastics material. The middle part 14 is preferably of a more flexible material than that of the parts 13 and 15. The upper and lower parts 13 and 15 may be flexible polyethylene foam, whilst the middle part 14 may be of flexible polyurethane foam. The abutting ends of the parts are of stepped configuration so as to fit together in plug and socket fashion. Thus the upper end of the lower part 15 has an inner upwardly projecting plug portion 15A, whilst the lower end of the middle part 14 has an outer downwardly projecting socket portion 14A, so that the parts can fit together as shown. The abutting ends of the middle part 14 and the upper part 13 are arranged in like manner, as shown. The joining planes 16 and 17 are inclined to the axis 18 of the leg, as shown. This provides that the rear portion 14B is longer than the front portion 14D.

In the region of the abutting ends, the abutting surfaces could be formed of harder, or even rigid, plastics material, for better interfitting of the three parts. The harder, or rigid, plastics material preferably would not extend to the outer surface of each of the three parts, so that the usual external shaping of the leg may be carried out as required.

It is desirable that the generally annular and axially extending meeting faces such as 14C and 15C at the abutting ends, should be slightly tapered, as shown, for ease of connection and disconnection.

Figure 2:
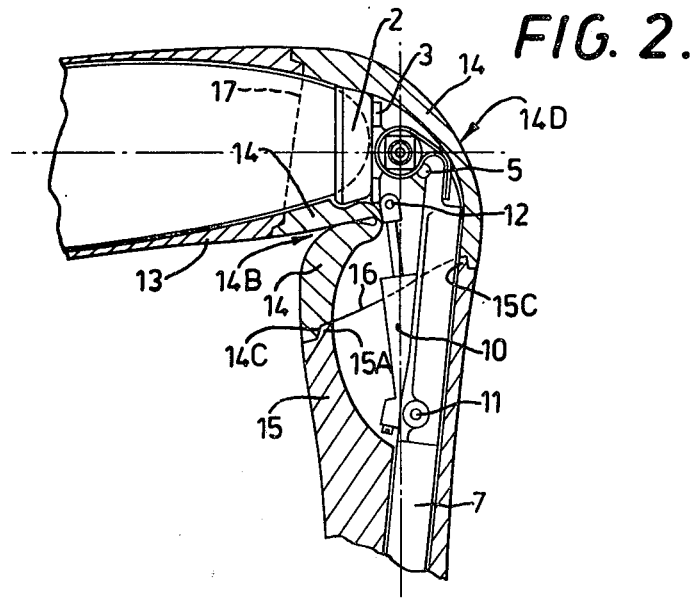
FIG. 2 shows the leg partly flexed.
Figure 3:
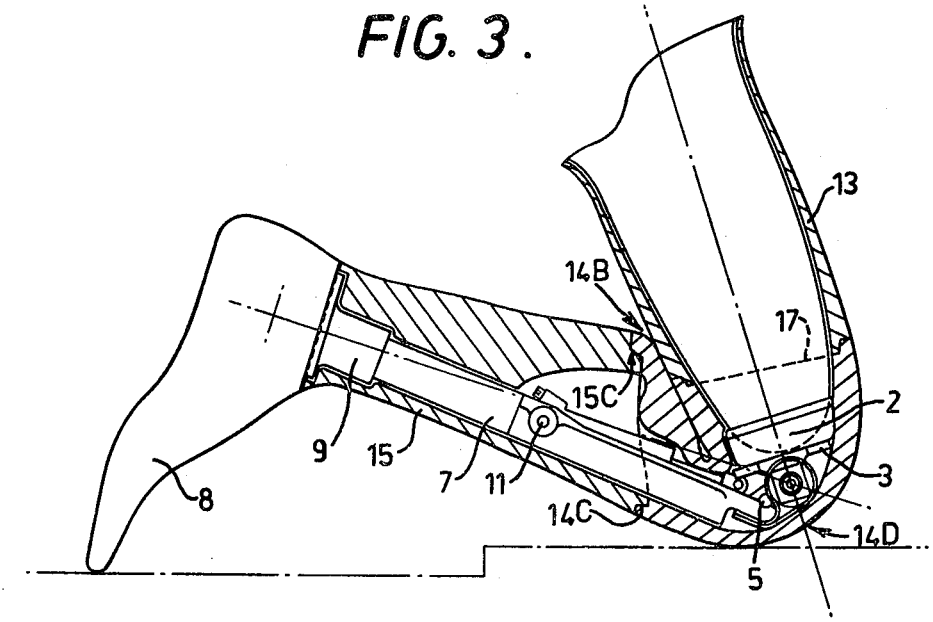
FIG. 3 shows the leg fully flexed.

FIG. 2 shows the leg partly flexed, that is, with the thigh and shin disposed at approximately 90°0to one another. It will be seen that that rear portion 14B is folded. FIG. 3 shows the leg fully flexed, with the portion 14B fully folded. The front portion 14D is stretched. It will be realized that with continual flexing of the leg about the knee pivot, the middle part 14 will become worn or damaged more quickly than the parts 13 and 15 which undergo little or no change of shape. Thus when the middle part 14 becomes worn or damaged, it may be removed and replaced. One method of removal and replacement of the middle part 14 would be to remove the foot 8, and then to slide the lower part 15 down over the shin tube 7 and adaptor 9, and then slide the middle part 14 also down over the shin tube and adaptor. A new middle part 14 could then be drawn up over the adaptor 9 and shin tube 7 and fitted over the upper part 13. The lower part 15 could then in turn be drawn up over the adaptor and shin tube, and be fitted into the lower end of the new middle part 14. The external surfaces could be finished and smoothed by removal of plastics material in the usual manner.

The invention thus offers the advantage that when the middle part 14 becomes worn, it alone has to be replaced, and not the whole covering, as was previously necessary with the known one-piece endo-skeletal outer covering. The invention also offers the advantage that the middle part 14 can be made of a different material from that of the upper and lower parts 13 and 15 respectively. Thus the middle part could be of a more flexible material, and the upper and lower parts can be made of a less expensive material. Also the middle part 14 can be shaped especially to the suitable as a knee covering. Another advantage is that a series of standard size middle, or knee covering, parts could be provided, so that the correct size for a particular patient could be selected, and would require only the minimum of the conventional finishing or shaping by removal of material from the external surface.

Although the mating planes 16 and 17 are shown as inclined to the axis 18, and this is the preferred arrangement, they could be at right angles to the axis 18.

In the embodiment, the foot is diagrammatically shown as being of the solid ankle type, that is, there is no ankle pivot. However, it would be possible to apply the invention to a leg having a foot connected to the shin by a conventional ankle pivot, in which case a fourth outer covering part could be provided. This fourth part could be for instance, like the middle part, of a flexible polyurethane foam, and could be removable and replaceable when worn.

Although the invention has been described above as applied to an artificial leg, it is also applicable to an artificial arm. Thus the upper part of the outer covering would enclose over the upper arm structure; the lower part of the outer covering would enclose the forearm structure; and the middle part would enclose the elbow joint.

In making the embodiment of artificial leg described above with reference to the attached drawings, the internal leg structure would first be assembled. This internal leg structure comprises thigh structure, in the form of the components 1 and 2, knee structure, in the form of the components 3, 4 and 5, a shin structure, in the form of the components 6, 7, 9 and 10. Before connection of the foot 8, the upper outer covering part 13 would be drawn on over the shin and knee structures, and applied to the thigh structure; then the middle outer covering part 14 would be drawn on, and applied to the knee structure; then the lower outer covering part 15 would be drawn on and applied to the shin structure. Also the three parts would be adjusted to abut accurately at their respective adjacent ends, that is, at the mating planes 16 and 17.

I claim:

1. An artificial leg of the endoskeletal type comprising: - a shin portion; a thigh portion; knee joint structure connecting together the shin portion and the thigh portion; a first tubular cosmetic covering on the shin portion; a second tubular cosmetic covering on the thigh portion; and an intermediate tubular cosmetic covering over the knee joint structure, the ends of the intermediate covering being in contact with the respective adjacent ends of the first and second coverings to avoid gaps between the coverings.

2. An artificial arm of the endoskeletal type comprising;- a forearm portion; an upper arm portion; elbow joint structure connecting together the forearm portion and the upper arm portion; a first tubular cosmetic covering on the forearm portion; a second tubular cosmetic covering on the upper arm portion; and an intermediate tubular cosmetic covering over the elbow joint structure, the ends of the intermediate covering being in contact with the respective adjacent ends of the first and second covering to avoid gaps between the coverings.

3. An artificial leg according to claim 1, wherein the coverings are of plastics material, that of the intermediate covering being different from that of the first and second coverings.

4. An artificial leg according to claim 3, wherein the intermediate covering is of a flexible polyurethane foam.

5. An artificial leg according to claim 1, wherein the ends of the intermediate covering interfit in plug and socket fashion with the respective adjacent ends of the first and second coverings.

6. An artificial leg according to claim 1, wherein the coverings are of plastics material and the surfaces of the said ends are formed on a plastics material that is harder than the plastics material of the remainder of the coverings.

7. An artificial leg according to claim 1, wherein the coverings are of plastics material and the surfaces of the said ends are formed on a plastics material that is rigid, the plastics material of the remainder of the coverings being non-rigid.

8. An artificial leg according to claim 1, wherein the first covering is of flexible polyethylene foam.

9. An artificial leg according to claim 1, wherein the second covering is of flexible polyethylene foam.

10. An artificial leg according to claim 1, wherein the respective said covering ends abut along planes which are inclined to the axis of the leg, such that the rear portion of the intermediate covering is longer than its front portion.

11. A method of making an artificial leg comprising the steps of providing connected shin, knee joint and thigh structues; applying a first cosmetic covering of tubular plastics material to the shin structure; applying an intermediate cosmetic covering of tubular plastics material over the knee joint structure; applying a second cosmetic covering of tubular plastics material to the thigh structure; and causing the three coverings to abut at their respective adjacent ends.

* * * * *